(12) United States Patent
Zagorchev et al.

(10) Patent No.: US 9,420,983 B2
(45) Date of Patent: Aug. 23, 2016

(54) SYSTEM FOR QUANTIFICATION OF NEOVASCULATURE IN CT VOLUMES

(75) Inventors: Lyubomir Zagorchev, Lebanon, NH (US); Andrew Buckler, Wenham, MA (US); Ravindra Bhat, Eindhoven (NL); Dennis E. Bos, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 958 days.

(21) Appl. No.: 12/739,833

(22) PCT Filed: Oct. 29, 2008

(86) PCT No.: PCT/IB2008/054485
§ 371 (c)(1),
(2), (4) Date: Apr. 26, 2010

(87) PCT Pub. No.: WO2009/060346
PCT Pub. Date: May 14, 2009

(65) Prior Publication Data
US 2010/0266190 A1 Oct. 21, 2010

Related U.S. Application Data

(60) Provisional application No. 60/988,571, filed on Nov. 16, 2007, provisional application No. 60/985,844, filed on Nov. 6, 2007.

(51) Int. Cl.
*G06K 9/00* (2006.01)
*A61B 6/00* (2006.01)
(Continued)

(52) U.S. Cl.
CPC .......... *A61B 6/503* (2013.01); *A61B 6/035* (2013.01); *A61B 6/504* (2013.01); *A61B 6/508* (2013.01); *A61B 6/583* (2013.01); *G06F 19/3406* (2013.01); *G06T 7/602* (2013.01);
(Continued)

(58) Field of Classification Search
CPC .......................... A61B 6/035; G06F 17/3406
USPC .................................. 382/128, 131
See application file for complete search history.

(56) References Cited

U.S. PATENT DOCUMENTS 4,922,915 A 5/1990 Arnold
6,104,775 A 8/2000 Tuy
(Continued)

OTHER PUBLICATIONS

T. Hildebrand, A. Laib, R. Muller, J. Dequeker, P. Ruegsegger, "Direct three-dimensional morphometric anaylsis of human cancellous bone: microstructural data from spine, femur, iliac crest, and calcaneus" J Bone Miner Res 14: 1167-1174, 1999.
(Continued)

*Primary Examiner* — Mark Holcomb
*Assistant Examiner* — Jason Tiedeman

(57) ABSTRACT

When quantifying neo-vasculature growth measured using a CT scanner (10), a known blood voxel is identified and adjoining voxels are compared thereto by a quantifier (52) to determine whether they are blood voxels, in order to grow a 3D image of the blood vessels. A removable Hounsfield calibration phantom (56) is positioned in a subject support (12) and concurrently scanned with the subject during each scan, and a Hounsfield unit calibrator (54) automatically calibrates acquired CT data to the phantom. A transport system comprising a plurality of movement-arresting locations facilitates cheaply and repeatably locking a CT detector (20), in six degrees of movement, at a plurality of locations in the scanner gantry.

15 Claims, 13 Drawing Sheets

(51) Int. Cl.
  *A61B 6/03* (2006.01)
  *G06F 19/00* (2011.01)
  *G06T 7/60* (2006.01)

(52) U.S. Cl.
  CPC ............... *G06T 2207/10081* (2013.01); *G06T 2207/30048* (2013.01); *G06T 2207/30096* (2013.01); *G06T 2207/30101* (2013.01)

(56) References Cited

U.S. PATENT DOCUMENTS

| | | | |
|---|---|---|---|
| 6,728,566 B1* | 4/2004 | Subramanyan | G06T 11/005 600/407 |
| 6,990,222 B2* | 1/2006 | Arnold | 382/131 |
| 7,024,027 B1* | 4/2006 | Suri et al. | 382/130 |
| 2004/0024295 A1* | 2/2004 | Cook | A61B 5/0059 600/310 |
| 2004/0252870 A1* | 12/2004 | Reeves | G06T 7/0012 382/128 |
| 2005/0113679 A1 | 5/2005 | Suryanarayanan et al. | |
| 2006/0088198 A1* | 4/2006 | Arnold | A61B 5/02007 382/131 |
| 2007/0019846 A1* | 1/2007 | Bullitt | G06T 7/0014 382/128 |
| 2007/0025527 A1* | 2/2007 | Eichenseer | A61B 6/0457 378/209 |
| 2008/0132774 A1* | 6/2008 | Milstein | G06T 7/0083 600/407 |
| 2009/0005693 A1* | 1/2009 | Brauner | A61B 6/508 600/481 |
| 2010/0159497 A1* | 6/2010 | Kimia et al. | 435/29 |

OTHER PUBLICATIONS

Tsutomu Tamada, Teruki Sone, Yoshimasa Jo, Shigeki Imai, Yasumasa Kajihara and Masao Fukunaga, "Three-dimensional trabecular bone architecture of the lumbar spine in bone metastasis from prostate cancer: comparison with degenerative sclerosis" Skeletal Radiology, vol. 34, No. 3, Mar. 2005, pp. 149-155.

W. Li, W. Shen, R. Gill, A. Corbly, B. Jones, R. Belagaje, Y. Zhang, S. Tang, Y. Chen, Y. Zhai, G. Wang, A. Wagle, K. Hui, M. Westmore, J. Hanson, Y.-F. Chen, M. Simons and J. Singh, "High-Resolution Quantitative Computed Tomography Demonstrating Selective Enhancement of Medium-Size Collaterals by Placental Growth Factor-1 in the Mouse Ischemic Hindlimb" Circulation, May 23, 2006; 113 (20): 2445-2453.

Daniela Tirziu, Karen L. Moodie, Zhen W. Zhuang, Katie Singer, Armin Helisch, Jeff F. Dunn, Weiming Li, Jaipal Singh and Michael Simons,"Delayed Arteriogenesis in Hypercholesterolemic Mice" Circulation 2005; 112; 2501-2509.

G. Wang et al., "A general conebeam reconstruction algorithm" IEEE Transactions on Medical Imaging, MI-12 (1993), pp. 486-496.

Boskamp, T., et al.; New Vessel Analysis Tool for Morphometric Quantification and Visualization of Vessels in CT and MR Imaging Data Sets; 2004; Radiographics; 24(1)287-297.

Gupta, R. K., et al.; Ralative cerebral blood volume is a measure of angiogenesis in brain tuberculoma and its therapeutic implications; 2006; Proc. In'l. Soc. MR in Med.; pp. 826.

Ritman, E. L., et al.; Micro-CT as a guide for clinical CT development; 2006; Proc. SPIE; vol. 6318; pp. 1-8.

Lorigo, et al., "Curves: Curve evolution for vessel segmentation", Medical Image Analysis, vol. 5, No. 3, Sep. 1, 2001, pp. 195-206.

* cited by examiner

SYSTEM FOR QUANTIFICATION OF NEOVASCULATURE IN CT VOLUMES

CROSS REFERENCE TO RELATED APPLICATIONS

This application claims the benefit of U.S. provisional application Ser. No. 60/985,844 filed Nov. 6, 2007 and U.S. provisional application Ser. No. 60/988,571 filed Nov. 16, 2010 both of which are incorporated herein by reference.

The present application finds particular application in medical imaging and treatment systems, particularly preclinical computed tomography (CT) imaging. However, it will be appreciated that the described technique may also find application in other imaging systems, other medical scenarios, or other medical techniques.

CT presents unique opportunities for highly quantitative three dimensional imaging of models of disease implanted or induced in animal models. It is a structural imaging modality that provides differentiation of contrast enhanced tissues, or structures with high attenuation factors, from non-enhanced soft tissues. Traditional applications of CT include screening for anatomical abnormalities and detection and quantification of anatomical changes in live animals or very small soft tissue samples removed from sacrificed animals. CT also starts to play an increasingly important role in angiogenesis, which is the process of formation of new capillary blood vessels (neo vasculature) as outgrowths of pre-existing ones. Angiogenesis occurs naturally during development, tissue repair, and abnormally in pathologic diseases such as heart ischemia, various tumors, and many others.

Parameters such as volume, area, connectivity, thickness, degree of anisotropy, are standard for analysis of trabecular bone microstructure (Hildebrand T, Laib A, Muller R, Dequeker J, Ruegsegger P. "*Direct three-dimensional morphometric analysis of human cancellous bone: microstructural data from spine, femur, iliac crest, and calcaneus*," J Bone Miner Res 14: 1167-1174, 1999 Tsutomu Tamada, Teruki Sone, Yoshimasa Jo, Shigeki Imai, Yasumasa Kajihara and Masao Fukunaga, "*Three-dimensional trabecular bone architecture of the lumbar spine in bone metastasis from prostate cancer: comparison with degenerative sclerosis*," Skeletal Radiology, Volume 34, Number 3, March, 2005, Pages 149-155) and were recently used for quantification of blood vessels (W. Li, W. Shen, R. Gill, A. Corbly, B. Jones, R. Belagaje, Y. Zhang, S. Tang, Y. Chen, Y. Zhai, G. Wang, A. Wagle, K. Hui, M. Westmore, J. Hanson, Y.-F. Chen, M. Simons and J. Singh, "*High-Resolution Quantitative Computed Tomography Demonstrating Selective Enhancement of Medium-Size Collaterals by Placental Growth Factor*-1 *in the Mouse Ischemic Hindlimb*," Circulation, May 23, 2006; 113 (20): 2445-2453 Daniela Tirziu, Karen L. Moodie, Zhen W. Zhuang, Katie Singer, Armin Helisch, Jeff F. Dunn, Weiming Li, Jaipal Singh and Michael Simons, "*Delayed Arteriogenesis in Hypercholesterolemic Mice*," Circulation 2005; 112; 2501-2509). The morphometric parameters in those studies, however, were computed after dimensional reduction of the 3D CT volumes to 2D sections or slices and parameters such as vessel diameter and volume were eliminated from the 2D sections. The studies are inaccurate because depending on the orientation of the imaged subjects and on how the 2D sections were obtained, e.g., a relative orientation of the section and a plane normal to an axis of a vessel, the resulting morphometric parameters (such as vessel diameter for example) would produce completely different results.

With regard to conventional methods for scanner calibration, Hounsfield unit calibration has to be performed manually. A phantom with known attenuation properties is scanned with each selectable imaging protocol (scan setting). The user has to manually define and select sub-volumes of interest in the phantom representing air, water, and bone. Then the software uses the average intensity values from the manually-defined sub-volumes to perform gray-scale/intensity to Hounsfield number mapping. This is a major disadvantage in preclinical systems in which non-standard imaging protocols are commonplace. Researchers frequently adjust or tweak the scan settings. Phantom-based recalibration for each adjustment is time consuming, requires a lot of manual user interaction, and slows down the imaging cycle.

With regard to CT image quality, small animal in-vivo imaging provides unique opportunities for imaging models of disease implanted in genetically altered animals. In particular, CT presents unique opportunities for highly quantitative three dimensional imaging of models of disease implanted or induced in animal models repeatedly over time to study disease or treatment evolution. It is a structural imaging modality that provides differentiation of contrast enhanced tissues, or structures with high attenuation factors, from non-enhanced soft tissues. Detector position accuracy and stability are important in order to be able to obtain good image quality. Typical solutions to obtain a variable detector position depend on high precision sliders for position accuracy and repeatability.

Traditional applications of CT include screening for anatomical abnormalities and detection and quantification of anatomical changes in live animals or very small soft tissue samples removed from sacrificed animals. CT also starts to play an increasingly important role in angiogenesis, which is the process of formation of new capillary blood vessels (neo vasculature) as outgrowths of pre-existing ones. Angiogenesis occurs naturally during development, tissue repair, and abnormally in pathologic diseases such as heart ischemia, various tumors, and many others.

One of the more demanding applications is in the field of oncology, where small animal imaging is used to assess the effect of a treatment in a given scenario as similar as possible to one that is clinically relevant. Current small animal models often rely on such procedures as implanting homogeneous cell lines on the flank and watching for tumor growth or shrinkage. Clinically relevant measures include quantifying metastasis in internal tissues, which requires high lesion detectability which in turn requires increasing image quality for a given field of view in the scanner.

All of the above has motivated the need for a fast, accurate, and robust system for quantification of neo vasculature in CT volumes, which provides a standard for the quantification of neo vasculature and currently does not exist on commercially available small animal imaging scanners. The present application provides new and improved systems and methods that facilitate neo-vasculature quantification, automatic Hounsfield unit calibration, and detector locking mechanisms that improve image quality, which overcome the above-referenced problems and others.

In accordance with one aspect, an imaging system includes a CT scanner that acquires CT data of a subject via and X-ray source and an X-ray detector, a reconstruction processor that reconstructs acquired CT data into a 3D image representation comprising a plurality of voxels, and a quantifier that quantifies new vascular growth in the subject by determining which voxels in the 3D image representation correspond to blood.

In accordance with another aspect, a method of performing neo-vasculature quantification in a subject includes acquiring CT data of the subject, reconstructing the CT data into 3D image representation having a 3D array of voxels, each voxel having a gray-scale value, identifying voxels corresponding to blood, and generating a 3D volume image of vasculature in the subject from the identified blood voxels.

In accordance with yet another aspect, a system for calibrating a CT scanner includes a subject support with a calibration phantom positioned therein, the calibration phantom including an air, a water, and a bone equivalent material at predetermined locations relative to the subject support, a detector that detects X-rays that have passed through an examination region, and a reconstruction processor that reconstructs a 3D image representation of a subject in an examination region. The system further includes an X-ray source that emits X-rays across the examination region to the X-ray detector, generating a field of view through the subject, the subject support, and the calibration phantom, and a calibrator that uses voxel values of the 3D image representation corresponding to the air, water, and bone equivalent material to calibrate the voxel values of the voxels of the 3D image representation to Hounsfield units (HU).

In accordance with another aspect, a system for arresting movement of an X-ray detector in six directions includes an X-ray detector that is slidably movable through a gantry in a CT scanner, a plurality of arresting elements coupled to one of the X-ray detector and the gantry, and a plurality of sets of arresting spheres or cylinders coupled to the other of the detector and the gantry, each set having an orientation complementary to an orientation of the plurality arresting elements on the detector. Each arresting element has a groove that receives an arresting sphere of a given set of arresting spheres or cylinders, and each groove is angularly offset relative to the grooves on the other arresting elements.

According to yet another aspect, a method of calculating growth of neo-vasculature, includes locking an X-ray detector in a predetermined position, generating a first volume image of a VOI, and performing a first neo-vasculature quantification to determine a first neo-vasculature volume. The method further includes allowing a predefined time period to lapse, positioning the detector in the same locked position, generating a second volume image of a VOI, performing a second neo-vasculature quantification to determine a second neo-vasculature volume, and determining a change in neo-vasculature volume by comparing the first and second neo-vasculature volumes.

One advantage is that neo-vasculature quantification speed and accuracy are increased.

Another advantage resides in reduced Hounsfield calibration time.

Another advantage resides in a cost-effective detector positioning mechanism.

Still further advantages of the subject innovation will be appreciated by those of ordinary skill in the art upon reading and understanding the following detailed description.

The innovation may take form in various components and arrangements of components, and in various steps and arrangements of steps. The drawings are only for purposes of illustrating various aspects and are not to be construed as limiting the invention.

Figure 12:
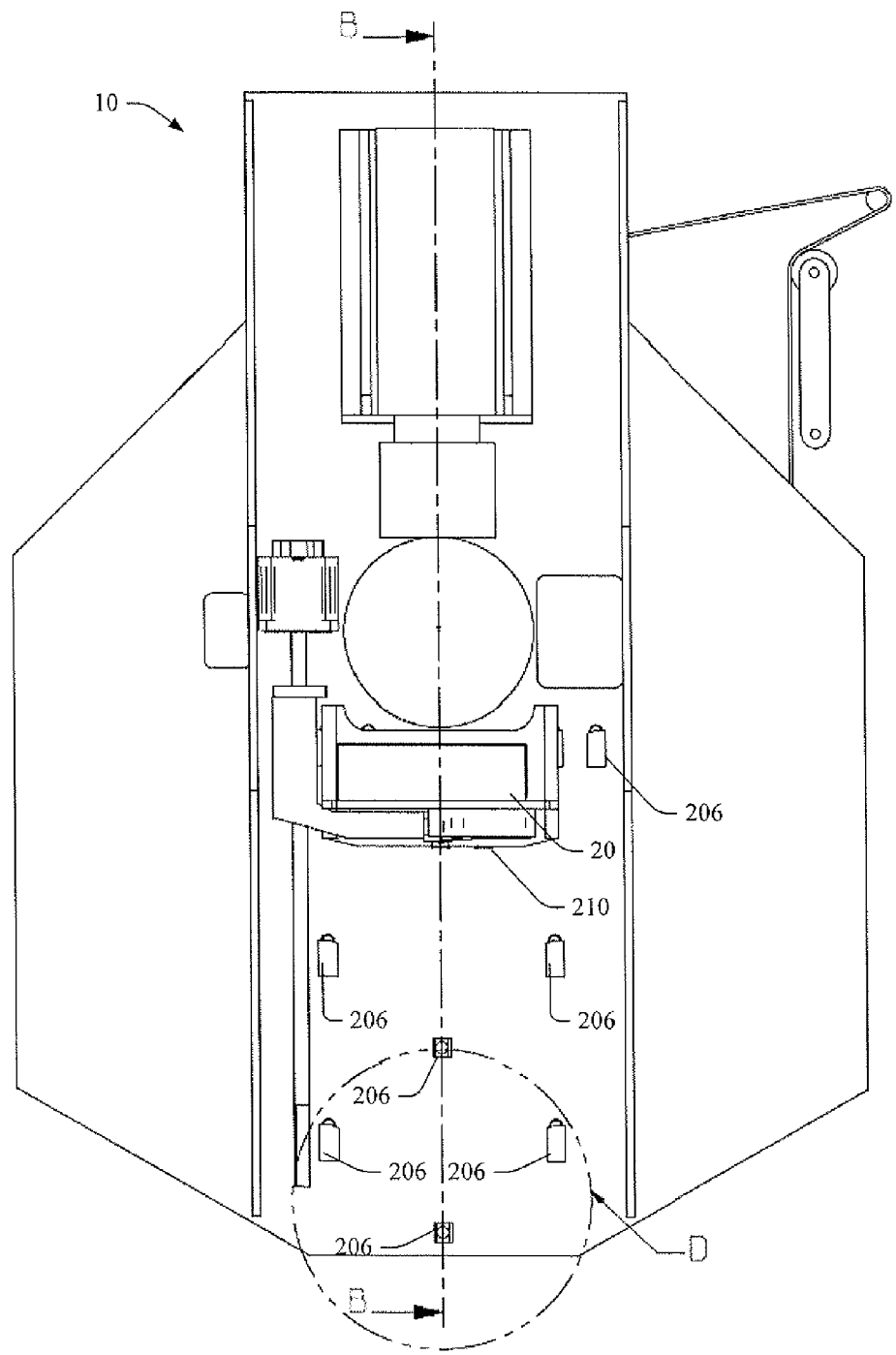

FIG. 12 diagrammatically illustrates a top-down view of the CT scanner, in which the transport system can be employed.

Figure 13:
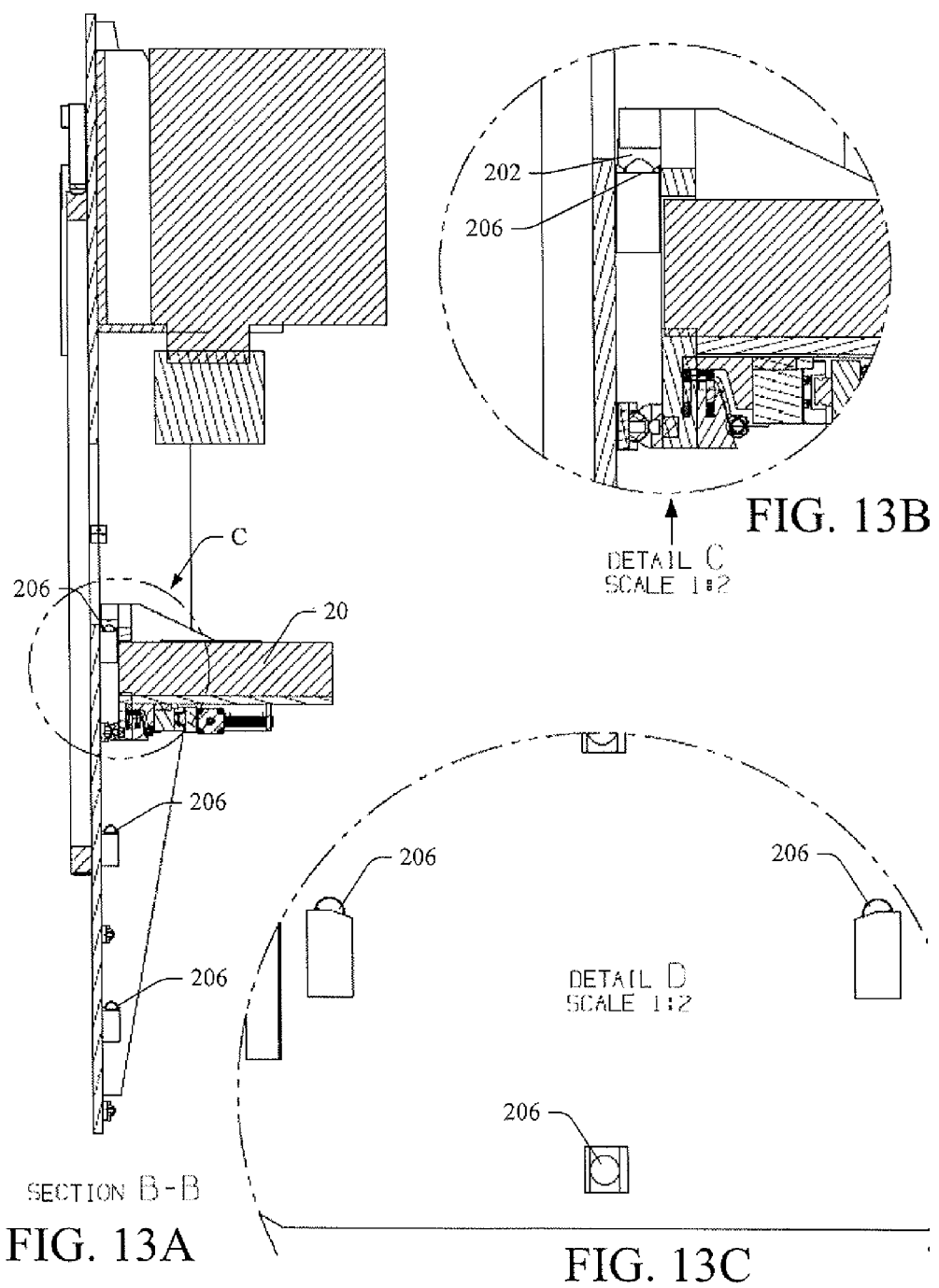

FIG. 13A illustrates a view of the scanner through the cut-plane "B-B."

FIG. 13B is a detached view of region C of FIG. 13A.

FIG. 13C is a detailed view of region D of FIG. 12.

Figure 14:
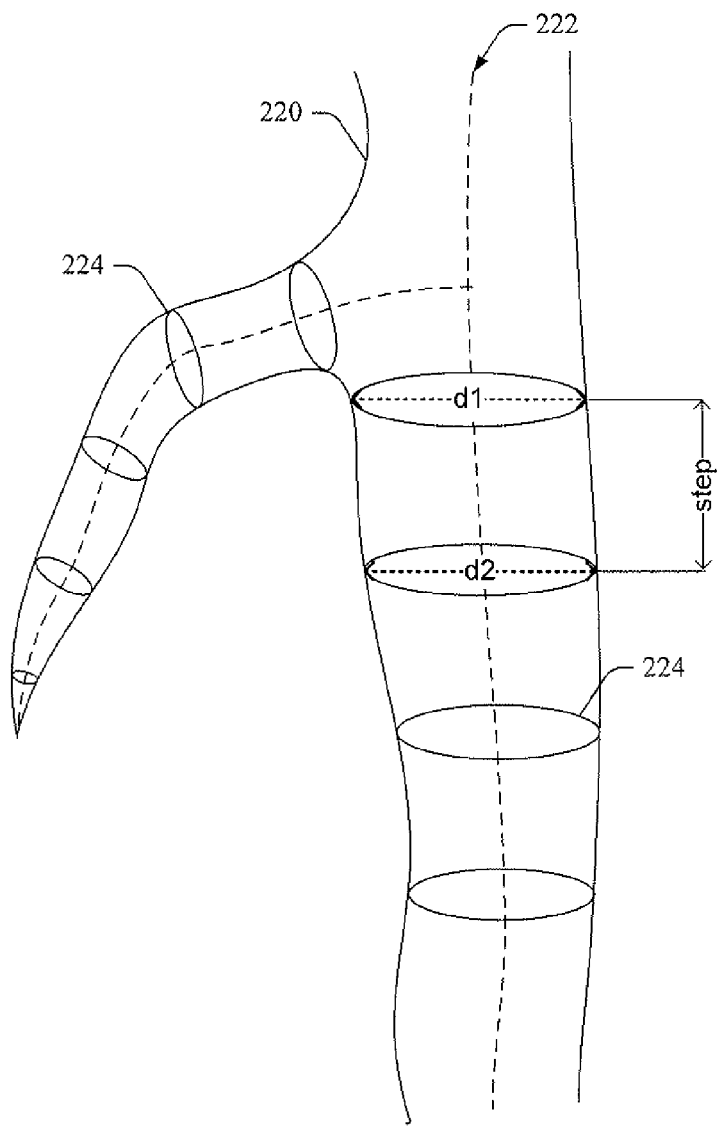

FIG. 14 is an illustration of neo-vasculature wherein a medial axis has been defined, and a plurality of measurement locations are shown.

Figure 15:
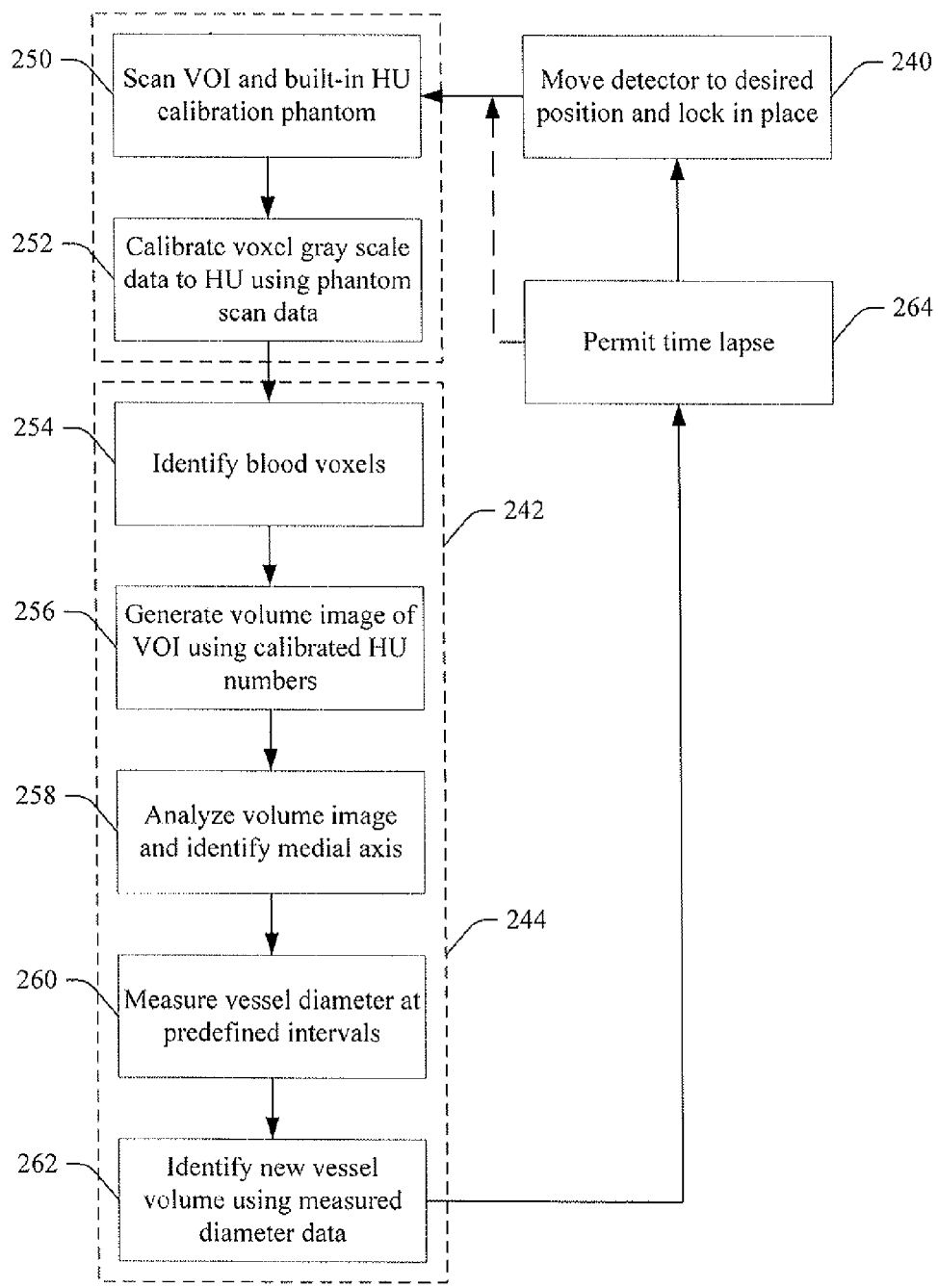

FIG. 15 illustrates a method for automatically calibrating CT scan data to HU numbers, quantifying new blood vessel growth, and locking an X-ray detector in one of a plurality of arresting positions in a gantry to which the detector is mounted.

Systems and methods are disclosed herein for quantifying new vasculature growth, automatically calculating Hounsfield units (HU) for scanner calibration, and lockably positioning an X-ray detector in variable positions. In preclinical cancer research, the growth of new vessels or neo vasculature in and surrounding a tumor is of considerable interest. When evaluating various treatments, researchers often want to evaluate the neo vasculature.

Figure 1:
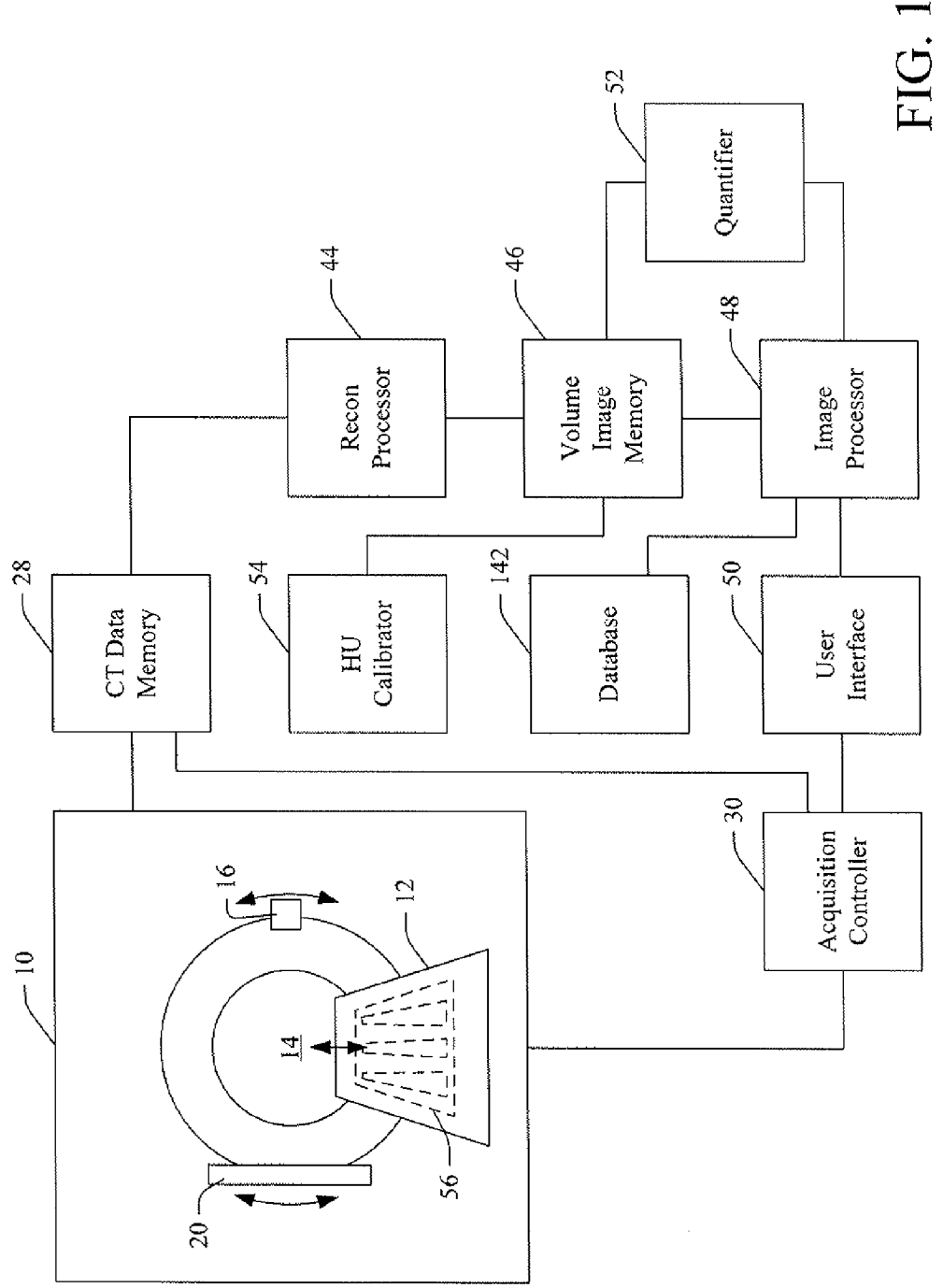
FIG. 1 illustrates an exemplary CT scanner that includes a subject support such as a patient couch which is linearly movable inside an examination region.

FIG. 1 illustrates an exemplary CT scanner 10 that includes a subject support 12 such as a patient couch which is linearly movable inside an examination region 14. In another embodiment, the subject support is stationary and the CT scanner moves linearly along and rotationally around the support. An x-ray tube assembly 16 mounted on a rotating gantry projects x-rays through the examination region 14. A collimator (not shown) collimates the radiation in one or more dimensions. In the exemplary CT scanner 10, an x-ray detector array 20 is disposed on the rotating gantry across the examination region from the x-ray tube. As described below, the detector is repositionable radially to adjust magnification and tangentially to adjust field of view (FOV). In an alternative embodiment (not shown), the detector array includes an array of two-dimensional detector rings mounted in a stationary fashion around the rotating gantry.

In one embodiment of the CT scanner 10, the x-ray tube assembly 16 cooperates with the collimator to produce a conical or wedge-shaped beam that diverges conically as it passes through the examination region 14. The cone beam substantially covers the detector array 20, which in a suitable embodiment includes sixteen rows of 1-10 mm detectors. It will be recognized that in the cone-beam geometry the x-ray paths to the various elements of the detector array 20 are not generally parallel. In another embodiment (not shown), a plurality of substantially parallel fan beams of radiation are generated, with each parallel beam detected by a corresponding row or rows of detectors. In one implementation of this embodiment, four detector rows are employed. More detector rows can be accommodated by using an x-ray tube with a multiple-anode assembly.

Regardless of the detailed geometry of the x-ray beam and the detector array 20, the x-ray detectors 20 operate in known ways to convert x-rays that have traversed the examination region 14 into electrical signals indicative of x-ray absorption between the x-ray tube 16 and the detectors 20. A patient (not shown) is positioned via the patient support 12 with the tumor or other region of interest (ROI) within the examination region 14 such that the x-ray beam passes through the ROI and associated vasculature.

The x-ray absorption signals, along with information on the angular position of the rotating gantry and the longitudinal position of the patient support 12, are communicated to a CT data memory 28. An acquisition controller 30 communicates with the CT scanner 10 to control CT scanning of the subject. The CT scanner 10 acquires projection data with a plurality of viewing angles by rotating the gantry that carries the x-ray source 16 and detector 20. Scanning in the z-direction is performed by moving the patient linearly via the subject couch 12. In spiral or helical CT imaging, the subject support 12 advances simultaneously with the gantry rotation such that the data acquisition occurs using a spiral geometry respective to the patient. Spiral/helical CT has the advantage of continuous and rapid data acquisition.

The acquired CT projection data is stored in the CT data memory 28, with angular position of the cone and the longitudinal position along the subject. The CT data are input to a reconstruction processor 44. The reconstruction processor 44 reconstructs a three-dimensional image representation of the region of interest. The reconstructed image is stored in a volume image memory 46. The reconstruction processor 44 operates on a complete data set constructed from the data segments.

One suitable three-dimensional reconstruction is a modified wedge-rebinned reconstruction such as is described by U.S. Pat. No. 6,104,775 issued to Tuy. Another suitable reconstruction is a three-dimensional modified Feldkamp-type cone-beam reconstruction such as is described by G. Wang et al., "A general conebeam reconstruction algorithm", IEEE Transactions on Medical Imaging, MI-12 (1993), pp. 486 496. Other three-dimensional reconstruction techniques can also be employed in the reconstruction processor 44.

With regard to automatic Hounsfield calibration, the gray scale value of a CT image is indicative of the amount of radiation which was absorbed by each voxel. However, analogous to a film camera in which the film may be over- or under-exposed, the gray scale value of a given voxel does not tell the viewer to a certainty how much radiation was absorbed by the given voxel. Rather, it only provides an indication of the relative amount of absorption relative to the other voxels of the image. This gray scale value can be calibrated to an absolute scale, known as the Hounsfield scale, in which air has a CT number of −1000, water 0, bone +400 to +1000, etc. This correlation is conventionally determined by conducting a preliminary scan using the same protocol, including the same scanner settings, on a phantom which includes a section of water, a section of air, and a section of bone with a known Hounsfield number, e.g., +1000. From the image of this phantom, the correlation between gray scale and Hounsfield number for the current protocol and scanner settings can be determined. A typical clinical scanner may have a large number of protocols, but they are preselected or fixed. Each of the protocols typically has been previously calibrated to the Hounsfield number using the above-described phantom "prescan." In preclinical work where the protocols are frequently customized, the scan is delayed or interrupted to perform phantom calibration for each new customized protocol.

Figure 2:
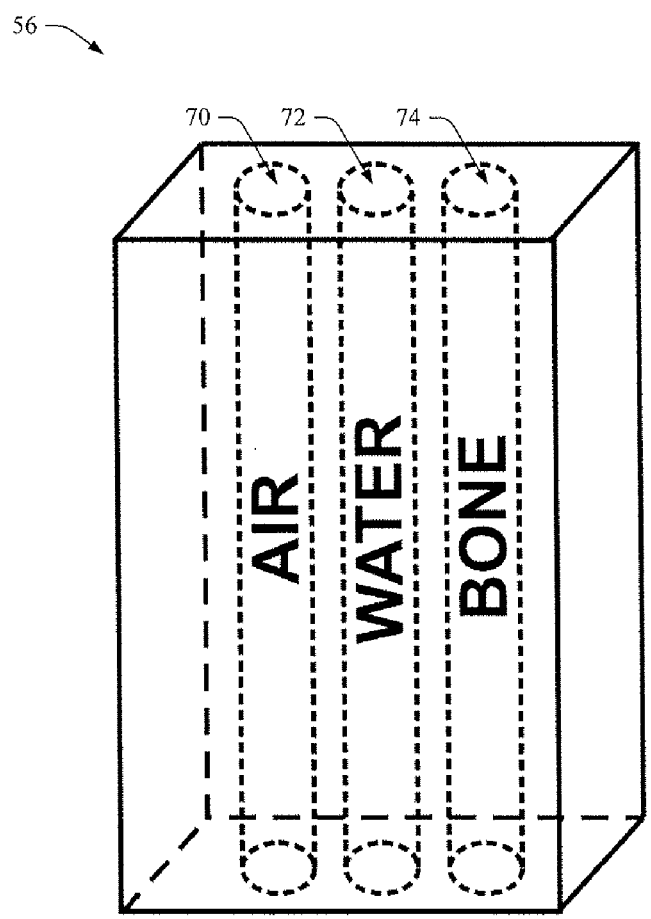
FIG. 2 illustrates an embodiment of the HU calibration phantom containing cylinders with air, water, and bone-equivalent material.

A calibration phantom 56 is removably inserted into the support 12 of the scanner. FIG. 2 illustrates an embodiment of the HU calibration phantom 56 containing cylinders with air, water, and bone equivalent materials. Three cylinders containing materials with known attenuation properties, such as air 70, water 72, and bone 74 can be easily embedded in a transparent parallelepiped made of acrylic, which has the attenuation properties of water, does not cause scatter, and will not interfere with other imaging modalities, in case of multimodal applications. In this manner, when the subject is scanned, the calibration phantom is scanned concurrently. Moreover, because the location of the calibration phantom is known, a Hounsfield calibrator 54 has instant access to the gray scale values of air, water, and bone and can quickly recalibrate the reconstructed image to Hounsfield numbers. Since the phantom is removable, it may optionally be replaced with a dose measuring device (not shown) which integrates the amount of radiation received and calculates the dose of radiation which the subject received during each examination. These radiation dose values represent another variable to be taken into account when evaluating treatments.

Returning now to FIG. 1, the reconstructed Hounsfield-calibrated image is advantageously processed by an imaging processor 48, which selects slices, generates maximum intensity images, generates volume-rendered images, or the like, and displayed on a user interface 50. In a typical preclinical CT apparatus, the user interface 50 also allows a clinician, diagnostician, or other user to select, create, modify scan parameters, or execute the selected/modified scanning program that directs the acquisition controller 30.

Those skilled in the art will be able to make further modifications of the system of FIG. 1 to suit particular applications. For example, the user interface 50 can include other components, such as printers, network connections, storage units, and the like (not shown), to facilitate efficient manipulating of the CT scanner 10.

A neo-vasculature quantifier 52 (e.g., a processor) segments the blood vessels from the remaining tissue. This can be done, for example, by finding one or more voxels which are known to be blood. The blood voxels can be identified manually (e.g., user-selected blood voxel using the user interface) or if the image data has been calibrated to Hounsfield numbers or units automatically by looking for one or more voxels having a Hounsfield unit (HU) that corresponds to blood. Once one or more blood voxels are identified, adjoining voxels are compared with it to find other voxels representing blood. As this process continues, the region occupied by blood grows forming a 3D image of the vessels.

Quantification is important for reliable evaluation of acquired data such as the estimation of vessel density and volume, which are the two primary indicators for the outcome of studies aimed at investigating the rate of progression of disease, effect of treatment, speed of recovery, etc. The added value of the three dimensional information about the structure of neo vasculature from CT volumes allows for comparisons to be made more easily, for detection of biological variation between subjects, and for more accurate diagnosis of disease. In addition, quantitative data is easily stored and analyzed, and numerical models are more straightforwardly constructed, which in turn advances the scientific experimentation.

Diameters of the vessels are determined by stepping along a medial axis of each vessel in regular intervals (e.g., 1 mm or so) and determining a diameter of the vessel at that point. Typically, a plane perpendicular to the medial axis can be used to find the cross section of the vessel. Because the size of each voxel is known from the CT scanner geometry, quantitative measurements of diameter can readily be made, for example by counting a number of blood voxels intersected by the plane. A circle-defining algorithm can be used to refine the cross-section for a more accurate calculation of the diameter or radius of the vessel at each point. The vessel diameter can be utilized to distinguish neo-vascular tissue from arteries (which are larger in diameter) and capillaries (which are smaller in diameter). Data from capillaries or arteries can be discarded. The region-growing process can be terminated at points in which the diameter of the vessel becomes too large or too small. This feature is described in greater detail with regard to FIG. 14.

One meaningful diagnostic output is a histogram of diameters versus blood vessel count. For example, if diameters are determined at 1 mm steps along the medial axis, the histogram can represent the number of measurement locations at which each diameter is located. The histogram can be used to determine whether a given blood vessel count (e.g. a number of steps or points at which vessel diameter is measured) is within a predetermined range of diameter values, above which the vessel is likely to be an artery or below which the vessel is likely to be a capillary.

Another meaningful measurement that can be performed and/or analyzed by the quantifier 52 is blood density. For instance the volume of a tumor and its neo-vasculature is readily determined from the voxel sizes. Similarly, the total volume of blood in the area of the tumor can be determined from the number of voxels that are identified as blood or from the geometry of the determined blood vessels. Additionally, a three-dimensional rendering of the vasculature can be generated by the reconstruction processor 44. Once the neo-vasculature has been defined, a standard surface rendering technique, such as triangulation, can be utilized by the image processor 48 to define the surface of the vessels. Once the surfaces are defined, a volume surface rendering can be displayed on the interface 50. The volume can be rotated to permit a researcher to examine the 3D rendering of the neo-vasculature from different directions.

The Hounsfield calibrator 54 performs various functions to calibrate micro-CT volumes to ensure reproducible results independent of the imaging protocol are disclosed herein. Hounsfield calibration provides a mapping for any micro-CT acquisition and depends on the parameters of the imaging protocol. A slight change of the imaging parameters can require a new calibration, which currently has to be performed manually, involves a lot of user interaction, and slows down the imaging cycle. By using the Hounsfield calibration phantom 56 (FIG. 1) for automatic calibration, manual user interaction is made unnecessary.

During micro-CT image acquisition, a beam of x-rays (e.g., from the X-ray source 16) passes through an object and the object attenuates the beam. The beam of x-rays is reduced in intensity as individual photons are absorbed or scattered by the object. The process is similar to the way that light passes through a translucent object. If light is shone through glass, most of the light comes through to the other side. Very little is absorbed or scattered by the glass. If light is shone through thick fabric, only a small amount of light will come through. The rest will be reflected back, absorbed, or scattered.

When projections of an object are created, the values of voxels are given in arbitrary digital units, usually stored as a "double" data type, which provides greater precision than other data types (e.g., integer or the like). The same material, however, may be given a different arbitrary value in another scan, because the scale depends on the particular scan and changes with variation of the parameters of the imaging protocol. As a result, if the same object is imaged with two different protocols, the images will be different. In order to overcome this problem, when a volume is reconstructed, the arbitrary digital units are converted to normalized CT values. The CT value is a number that represents the attenuation coefficient of a particular voxel in the reconstruction and is given in Hounsfield units (HU).

Figure 3:
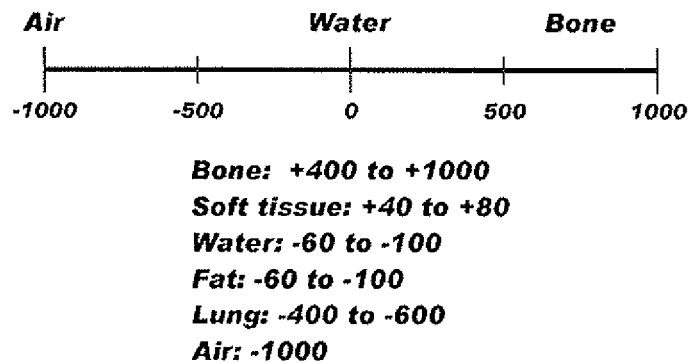
FIG. 3 illustrates a Hounsfield scale, which has specific known values for air and water, and wherein the CT values are calibrated appropriately using actual air and water (or equivalents) in a specific scan as reference points.

FIG. 3 illustrates a Hounsfield scale, which has specific known values for air and water, and wherein the CT values are calibrated appropriately using actual air and water (or equivalents) in a specific scan as reference points. The more reference points for comparison, the more accurate the mapping. Note, that the HU scale may extend up to 4000 for bone depending on the manufacturer. Air and water are at −1000 HU and 0 HU, respectively. By incorporating the three point HU calibration phantom 56 into the imaging bed or patient support 12, it becomes possible to perform the calibration automatically, overcoming limitations associated with conventional manual Hounsfield calibration (e.g., lengthy calibration time, etc.).

The HU calibrator 54 employs the HU calibration phantom 56, embedded in the patient support 12, to determine HU values for air, water, and bone during each scan. The HU calibrator then extracts sub-volumes of interest from the materials with known attenuation properties and calculates average values for air, water, and bone from the imaged volume. Automatic mapping of average units to CT units according to the HU scale is then performed.

Figure 4:
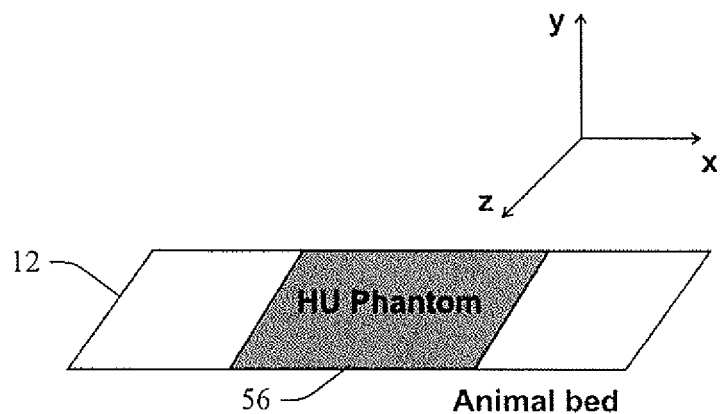
FIG. 4 illustrates one embodiment of the calibration phantom embedded or attached to an imaging bed or patient support.

FIG. 4 illustrates one embodiment of the calibration phantom 56 embedded or attached to an imaging bed or patient support 12. The phantom can be rigidly attached to the bed and can be retained in the field of view of the CT scanner 10 (FIG. 1). Knowing the exact geometry of the HU calibration phantom, such as dimensions, cylinder size, relative offset, along with the offset of the phantom from the coordinate origin of the bed, allows for automatic extraction of sub-volumes of interest from the cylinders containing air, water, and bone, and thus the automatic HU calibration by the HU calibrator 54. It is straightforward to implement all of the above in software, which can be executed automatically at or near the end of the micro-CT reconstructions. The end user will receive a calibrated volume with values mapped to the Hounsfield scale.

The phantom 56 can be detachable, so that it can be removed and replaced with transparent plastic piece or the like, if not needed for a particular acquisition. The same can be done if the imaging bed is interchangeable and can be used in another scanner, like micro PET, for example. By attaching the phantom under the bed, the animal can stay on the bed while the phantom is being attached or detached. In this way, the position of the imaging animal will remain the same during multimodal acquisitions and the phantom would interfere with neither the acquisition nor the imaged subject.

Another embodiment relates to the use of more than three materials for calibration. A greater number of reference points for comparison will result in more accurate mapping. With an automatic process this can be easily done.

Figure 5:
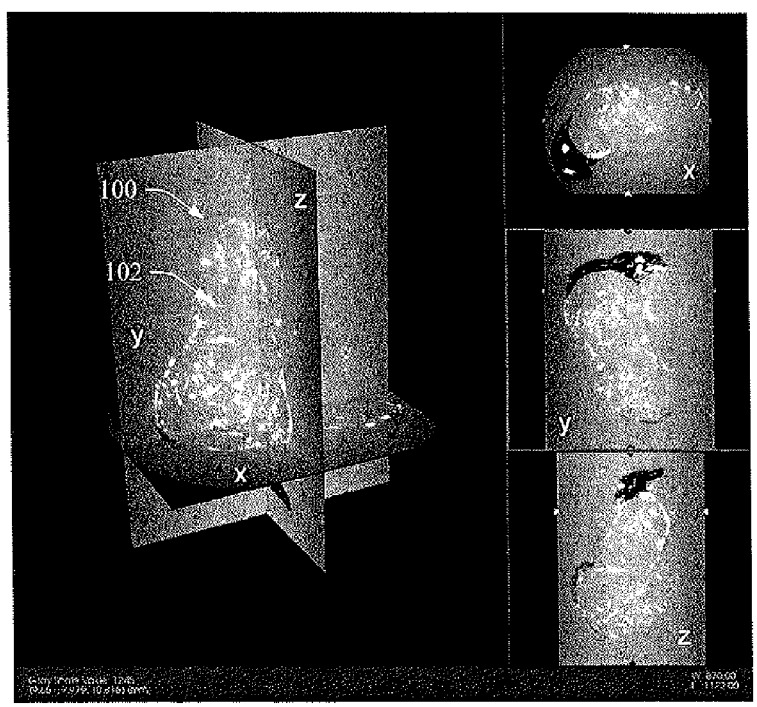
FIG. 5 is a screenshot of a CT volume of a pancreatic tumor harvested from the flank of an athymic mouse.

FIG. 5 is a screenshot of three orthogonal slices through a pancreatic tumor 100 harvested from the flank of an athymic mouse. The mouse was perfused with Microfil and imaged at 13 microns. The capillary blood vessels 102 appear in white on the three orthogonal cross-sections (x, y, and z) of the volume.

Figure 6B:
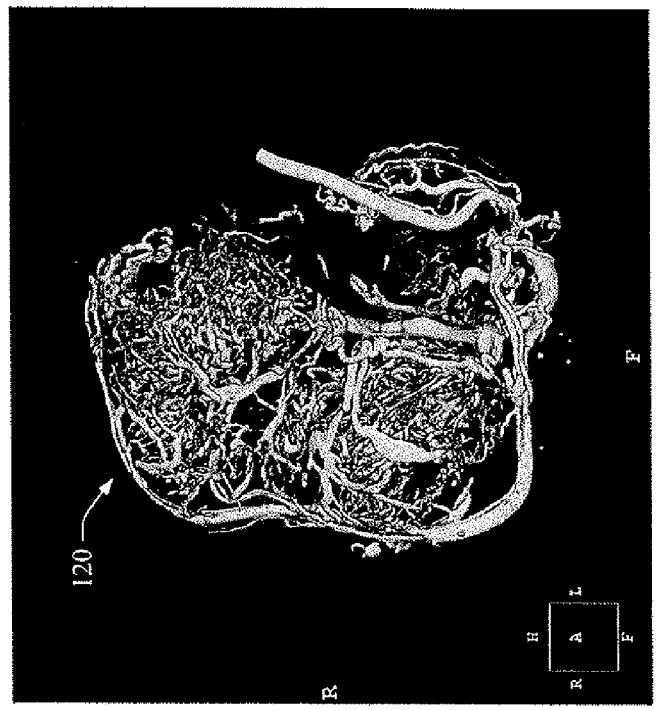
FIGS. 6A and 6B illustrate two alternative visualizations of the CT volume shown in FIG. 5: maximum intensity projection (MIP), and volumetric surface rendering, respectively.
Figure 6A:
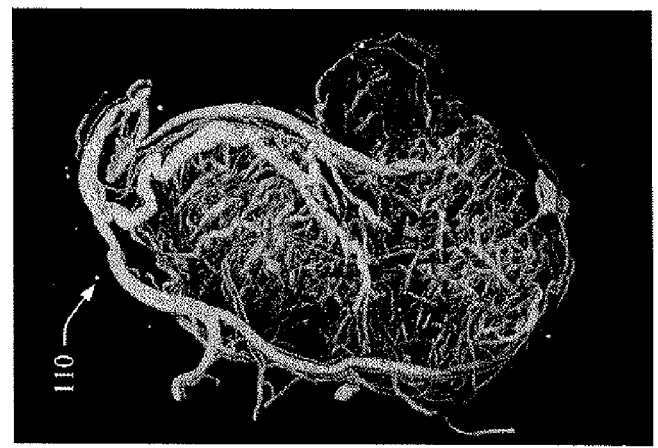

FIGS. 6A and B illustrate two alternative visualizations of the CT volume shown in FIG. 5: maximum intensity projection 110, and volumetric surface rendering 120, respectively. Despite their high resolution, CT volumes are often used for visualization of neo-vasculature by standard computer graphics techniques such as two-dimensional maximum intensity projections of the three dimensional CT volumes or volumetric surface renderings.

Since quantification is performed in the three dimensional volume, as opposed to 2D sections, the graphical user interface 50 visually depicts the optimal segmentation of the volume of interest and enclosed blood vessels in three dimensions achieved by appropriate volume rendering techniques. An example using the CT volume of the pancreatic tumor from FIG. 5 is shown in FIGS. 7A and B.

Figure 7A:
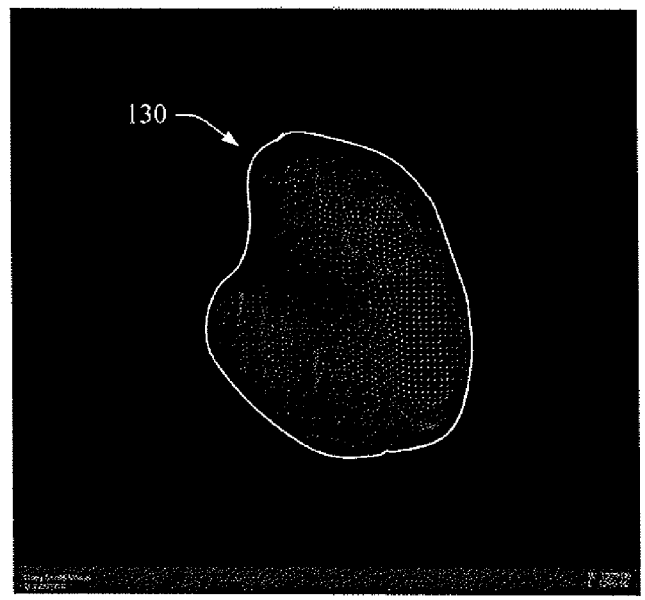
FIG. 7A illustrates a deformable mesh adapted to the boundaries of the tumor shown in 3D.
Figure 7B:
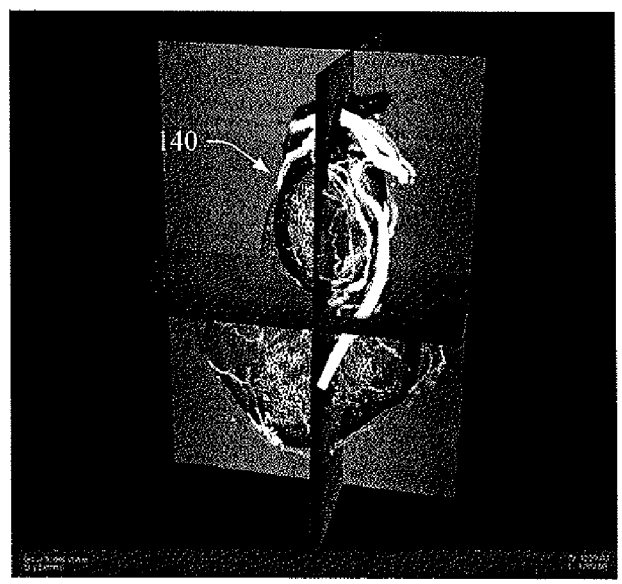
FIG. 7B shows the deformable mesh overlaid with the segmented blood vessels and three orthogonal texture mapped planes representing the CT volume.

FIG. 7A illustrates a deformable mesh 130 adapted to the boundaries of the tumor shown in three dimensions. FIG. 7B shows the deformable mesh overlaid with the segmented blood vessels and three orthogonal texture mapped planes representing the CT volume 140. A user can quickly navigate through the presented segmentation and modify the segmentation parameters, selecting an optimal three dimensional segmentation of both tumor and vessels. The system of FIG. 1 can also be connected to a database 142 of previous scans to identify studies with similar features and adaptively choose the best set of segmentation parameters according to prior knowledge. The database 142 can define the steps and settings for rapid and accurate quantification of CT volumes performed in three dimensional space by the image processor 48. It can also store the quantification results in a knowledge base for further hypothesis testing and statistical analysis.

Deformable segmentation techniques can be used to adapt a mesh 130 to the boundary of the imaged object. Prior information about the intensity variation on the object boundaries can be obtained from a set of manually segmented training data and incorporated in the deformation process. This enables the segmentation of the volume of interest containing the neo vessels. After the volume of interest is segmented, volume rendering techniques such as ray casting can be applied to the enclosed volume to segment out the blood vessels in 3D. Given the volume of interest enclosed in the deformed mesh, $V_{VOI}$, and the volume of blood vessels, $V_{VBV}$, the vessel density can be calculated as the ratio of blood vessel volume over the volume of interest: $V_{VBV}/V_{VOI}$.

Interactive modification of the segmentation can also be performed by the user based on previous subjects with similar features. Furthermore, the capability for 2D region of interest delineation and manual generation of 3D volumes of interest can be provided, which is useful in pathologic cases where standard automatic segmentation of the volume of interest cannot be obtained.

Figure 8:
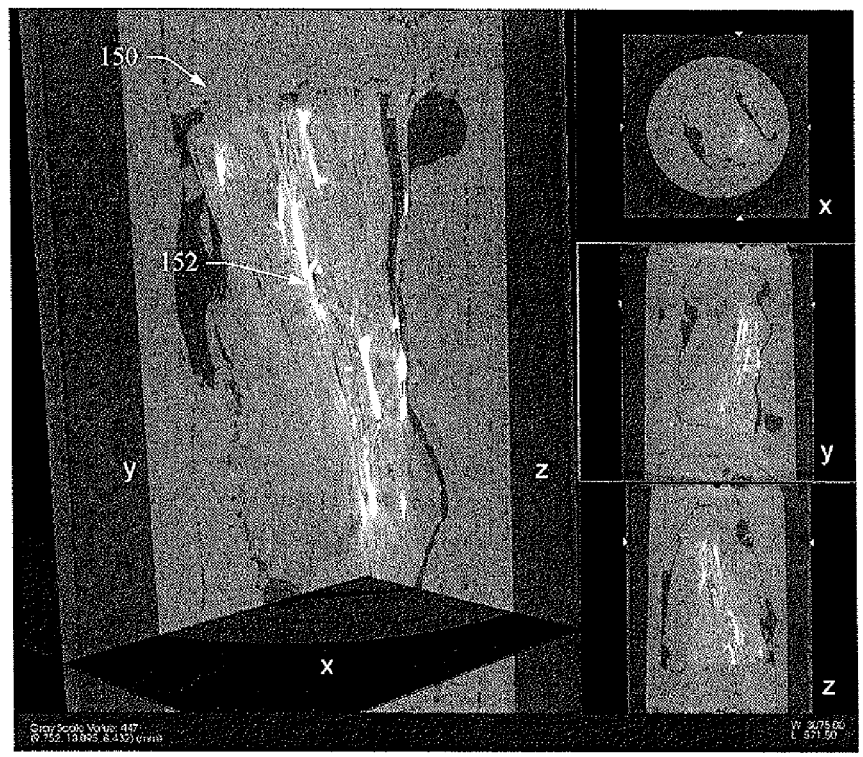
FIG. 8 is a screenshot of a texture mapping of a 3D micro-CT volume from a hind limb ischemia model in a mouse.

FIG. 8 is a screenshot of a texture mapping 150 of a 3D micro-CT volume from a hind limb ischemia model in a mouse. The mouse was perfused with 25% Bismuth and imaged at 28 microns. The blood vessels 152 appear in white on the three orthogonal cross-sections (x, y, z) of the volume.

In preclinical scanners, it is advantageous to be able to move the detector 20 close to the patient to minimize the receipt of scattered radiation and noise, and to move the detector further from the patient for magnification. Moreover, to increase the field of view, the detector can be shifted laterally such that the detector extends from the center line of the scanner laterally in only one direction. Such a detector placement doubles the field of view but results in only one data set being collected for 360° of rotation. In preclinical scanners which image with very high resolution (e.g., on the order of approximately 13 microns or so), accurate detector position becomes of paramount importance. When procedures are run a second time, e.g., to monitor the progress of a tumor or a treatment, it is important that the detector be positioned precisely in the same location. Even small variations in the detector placement can cause significant errors when subsequent images are compared with earlier images. To assure accurate placement of the detector, a fixed number of detector locations (e.g., a close position, a close offset position, a far position, and a far offset position, although more or fewer positions are possible) in which the detector can be locked are provided. The variable positions of the detector 20 are described in greater detail in FIGS. 9-13)

Figure 9:
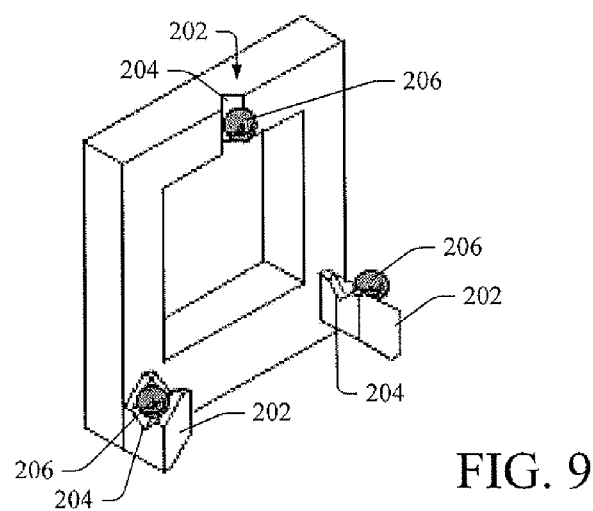
FIG. 9 illustrates a transport system that facilitates locking the X-ray detector of FIG. 1 in place during a scan without using expensive high-precision sliders.

FIG. 9 illustrates a system that facilitates locking the X-ray detector 20 of FIG. 1 in place during a scan without using expensive high-precision sliders. The system can be deployed in interior walls of a gantry (not shown) in a CT scanner such as the scanner 10. Each arresting location in the gantry includes a set of arresting elements 202, each comprising a groove 204, such that the three groves 204 of a given arresting location are orthogonal to each other. A plurality of small spheres (e.g., steel balls, bearings, or the like) are rotatably coupled to the detector (not shown). When the spheres mate with the grooves, each sphere is in contact with its groove at two points, resulting in arrested movement in 6 degrees (e.g., movement is locked in forward and backward directions in three orthogonal planes). The gantry has multiple sets of the 6 degree-of-freedom-arresting elements (one set for each geometry mode). In one embodiment, the detector is mounted on a part which is rigidly connected to the above shown three balls. Such an arrangement facilitates highly repeatable positioning of the detector.

Figure 10A:
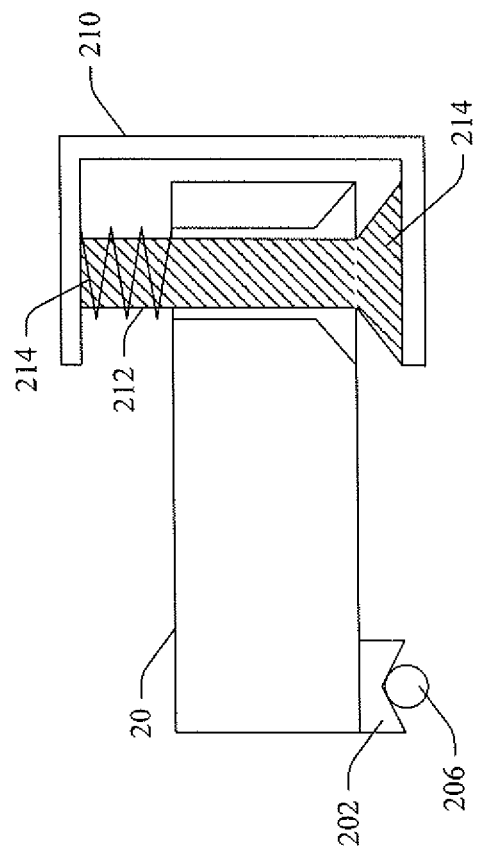
FIGS. 10A and 10B illustrate the transport system for a detector in a travelling state and in a stationary or locked state, respectively.
Figure 10B:
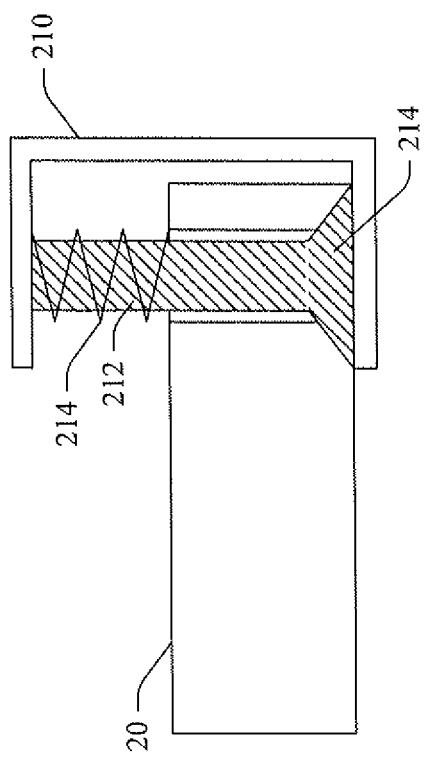

FIGS. 10A and 10B illustrate transport system for a detector 20 in a travelling state and in a stationary or locked state, respectively. For example, a slider 210 includes a mounting element 212 that passes through a portion of the detector to couple the detector to the slider. The slider can move up and down and to the side. The detector is supported on the slider by springs 214, or the like, such that it floats relative to the stage. At each of a plurality of preset detector positions, a set of mechanical arresting elements 202 directly support the detector such that it is fixed in all 6 degrees of freedom. More specifically, three v-shaped grooves 204 of appropriately selected different orientations mounted to one of the gantry and the detector (e.g., the detector in the illustration of FIG. 10B), and a spherical or cylindrical element 206 connected to the other. The springs on which the detector is mounted in a floating manner provide a preset biasing force between the grooves and the ball or cylindrical elements. By biasing these elements together such that each ball or cylinder from the contacts to surfaces of the groove, the detector is constrained relative to all 6 degrees of freedom.

Each detector position that is desired (e.g., each representing a useful geometry for the end-user, in this example there are three distinguished detector positions) uses a set of mechanical arresting elements 202. By pressing the detector against the arresting elements, the detector assembly is accurately and repeatably fixed in all 6 degrees of freedom. The design is such that the pressing force is delivered by the sliders, and incorporates a decoupling measure to prevent the sliders from determining the detector position when pressing the detector assembly against the arresting elements.

The slider thus includes low cost, non-precision elements (e.g., spheres in FIG. 9 and grooves in FIG. 10B that are interconnected to the detector assembly. The working principle of this interconnection is as follows: during transfer the detector is located on the cone 214 without any clearance, i.e. the detector is rigidly connected to the slider. However when positioned on one of the detector positions associated with the geometry modes, the detector is located by the sphere 206 (e.g., a steel ball or the like) and groove interaction, the detector comes off the cone 214, i.e. it will be free floating with respect to the transporter 210. The compression spring 212 provides the preloading.

Figure 11:
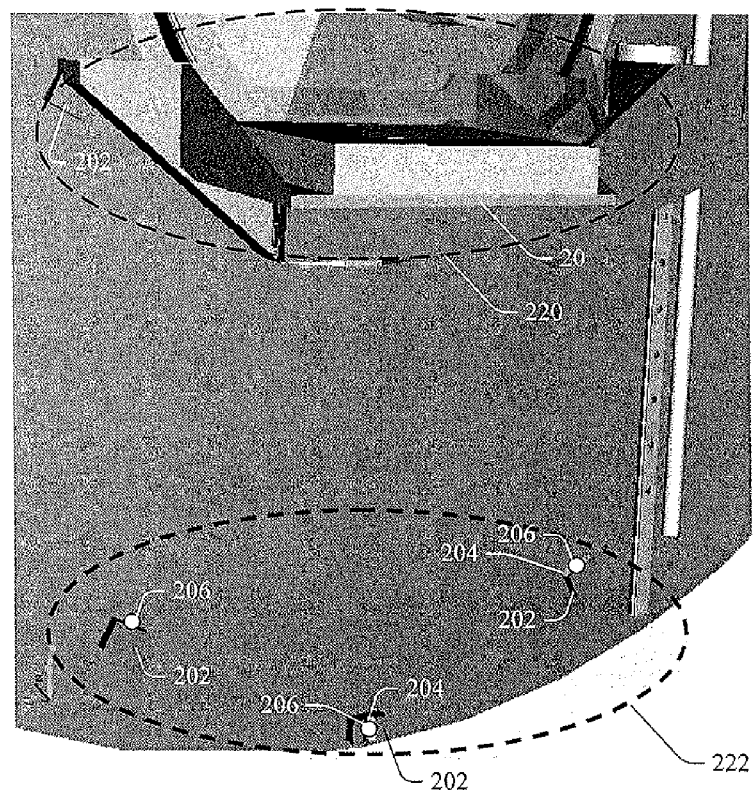
FIG. 11 illustrates an overview of the implementation of the transport system.

FIG. 11 illustrates an overview of the implementation of the transport system of FIGS. 9 and 10. One embodiment uses a variation of the locating principle shown in FIG. 9, namely two location elements on top and one at the bottom. The detector is locked in a first position 220. A second position 222 is also shown, where the detector can be moved to be locked into position via a plurality of arresting elements 202 comprising respective orthogonal grooves into which a corresponding spheres 206 on the detector are received when the detector reaches the second position. By introducing the geometry modes in a cost effective and repeatable manner, the transport system provides the flexibility of a system for imaging perfusion, tumor biology and angiogenesis, among many others.

FIGS. 12 and 13A-C diagrammatically illustrates a top-down view of the CT scanner 10, in which the transport system can be employed. In this embodiment, the grooves 204 are carriers by the detector and the spheres 206 are mounted on the gantry. A cut-plane "B-B" runs down the center of the gantry of the scanner and a detector 20 is locked in an arresting location. For example, the detector has coupled to it several (e.g., three) arresting elements (not shown), which are locked by the slider spring (not shown) against a plurality of spheres 206 mounted to the interiors of the scanner gantry.

FIG. 14 is an illustration of neo-vasculature 220 wherein a medial axis 222 has been defined, and a plurality of measurement locations 224 are shown. For example, the quantifier 52 (FIG. 1) can evaluate image data stored in the volume image memory 46 (FIG. 1), and identify a medial axis running through each of a plurality of portions of the neo-vasculature. In one embodiment, the medial axis is interpolated from the 3D vessel image as a central line running through the vessel.

The quantifier then identifies a plurality of measurement points along the vessel at which to measure vessel diameter. In one embodiment, the measurement points are equally spaced at a predetermined interval (e.g., tens or hundreds of microns, approximately one millimeter, etc., depending on a desired level of measurement granularity). Diameter measurements d1, d2, and so on, for respective measurement points are then stored to memory and analyzed by the quantifier, which compares the measured diameter information to a predefined rage of diameter values. If a predetermined number (e.g., one or more) of contiguous measurement points register a diameter that is outside of (e.g., larger or smaller than) the predefined range, then the quantifier can determine that the vessel portion registering such diameter(s) is part of an artery (if larger) or part of a capillary (if smaller), and therefore excluded from the neo-vasculature volume. The remaining portion of the blood vessel, which registers diameter values within the predefined range is then classified as neo-vasculature, and the new vessel growth is thus quantified.

FIG. 15 illustrates a method for automatically calibrating CT scan data to HU numbers, quantifying new blood vessel growth, and locking an X-ray detector in one of a plurality of arresting positions in a gantry to which the detector is mounted. Although described as a series of acts, it will be understood that fewer than all described acts may be required to perform the method in accordance with various examples described in this document. Moreover, other acts may be included in the method, such as are described with regard to the preceding figures. Furthermore, some acts may occur in an order different from the depicted order, as will be appreciated by those of skill in the art.

The method comprises a detector positioning protocol 240, a Hounsfield calibration protocol 242, and a neo-vasculature quantification protocol 244. Detector positioning 240 can include arresting detector movement in a gantry using the arresting elements and related components described in relation to preceding figures. Hounsfield calibration 242 can include concurrently scanning a VOI and an HU calibration phantom, at 250. The calibration phantom can include air, water, and bone equivalent materials to provide a reference frame for calibration. At 252, gray scale values associated with scan data are converted or calibrated to Hounsfield unit numbers using CT scan data acquired from the calibration phantom. A 3D image of the VOI can then be generated from the calibrated scan data.

Neo-vasculature quantification 244 includes, at 254, identifying blood voxels in a 3D image of the VOI. For example, a first blood voxel can be identified manually by an operator or can be automatically identified as a voxel having a Hounsfield number consistent with a Hounsfield number for blood. At 256, a volume image of the VOI can be generated using calibrated HU numbers (e.g., wherein voxels contiguous to a known blood voxel are analyzed to determine whether their HU numbers are consistent with the known blood voxel, iteratively, to define the volume).

Neo-vasculature quantification 244 further includes analyzing the volume image and defining a medial axis for one or more vessel portions or lengths in the volume image, at 258. At 260, blood vessel diameter is measured along a given vessel length at predefined intervals. Once all vessels in the image volume have been measured, vessel portions having diameter measurements outside of a predefined diameter range are discarded, and the remaining vessel portions are identified as neo-vasculature, at 262.

In one embodiment, the method is employed includes permitting a time lapse, at 264, between quantification iterations. For example, the time lapse can be on the order of days, weeks, months, etc., after which the method can be repeated, beginning with detector positioning, at 240 (e.g., in a same locked position as used in the previous CT scan). Alternatively, detector positioning can be omitted from both CT scans. In another embodiment, Hounsfield calibration is additionally or alternatively omitted, and the second iteration of the method permitting the time lapse at 264 followed by regenerating the volume image of the VOI. In any case, a second neo-vasculature volume is identified during the second iteration, and can be compared to the neo-vasculature volume image generated during the previous iteration to determine a change in volume size over the lapsed time period.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. An imaging system, including:
   CT scanner that acquires CT data of a subject via and X-ray source and an X-ray detector;
   a reconstruction processor that reconstructs acquired CT data into a 3D image representation comprising a plurality of voxels; and
   a quantifier that quantifies new vascular growth in the subject by determining which voxels in the 3D image representation correspond to blood;
   a calibrator that calibrates voxels of the 3D image representation to Hounsfield units (HU);
   wherein the quantifier:
      identifies voxels having a Hounsfield unit consistent with known Hounsfield units for blood, as blood voxels;
      generates a 3D blood vessel vasculature volume image;
      calculates a medial axis of vessels in the blood vessel volume image;
      steps along a blood vessel medial axis;
      at each step, measures a diameter of the blood vessel;
      generates a histogram of the number of steps with each measured diameter;
      generates a 3D expansion of the 3D vasculature image;
      compares each blood vessel diameter measurement with a predetermined blood vessel diameter value range that includes a lower level indicative of blood vessel diameter consistent with a predefined capillary diameter and an upper level indicative of blood vessel diameter consistent with a predefined artery diameter; and
      automatically terminates expansion of the 3D vasculature image along a given path when the number of laterally adjacent blood voxels falls outside the predetermined blood vessel diameter value range; and
   a display that displays a 3D volume rendering of the 3D volume image representation of the vasculature;
   wherein the reconstruction processor automatically generates the 3D volume rendering of the 3D volume image representation of the vasculature upon termination of expansion of the 3D vasculature image by the quantifier.

2. The system according to claim 1, wherein a user identifies a blood voxel in a 3D image of the subject on the user interface, and the quantifier compares the identified blood voxel with neighboring voxels to identify additional blood voxels, which are compared with neighboring voxels to iteratively map a vascular system.

3. The system according to claim 1, wherein the quantifier determines a ratio of blood vessel volume from a volume of a tumor in the 3D image representation and a number of blood voxels in the tumor volume.

4. The system according to claim 1, wherein the quantifier:
   calculates a volume of the blood vessels;
   calculates a volume of a volume of interest; and
   calculates a ratio.

5. The system according to claim 1, further including:
   a Hounsfield calibration phantom positioned in a subject support on which the subject is positioned, wherein the phantom is scanned concurrently with the subject.

6. The system according to claim 5, wherein the phantom further includes each of air, water, and bone equivalent materials, each at fixed locations in the subject support.

7. The system according to claim 6, further including further including:
   a Hounsfield unit calibrator that:
      determines voxels in the 3D image representation corresponding to each of the water, air, and bone equivalent materials; and
      based on intensity values of the determined voxels, calibrates the 3D image representation to Hounsfield units (HU).

8. The system according to claim 1, wherein the CT scanner further includes:
   a gantry that defines an examination region about the subject support; and
   a plurality of arresting elements, mounted on one of the gantry and a detector, that mate with sets of arresting spheres or rods positioned on the other one of the gantry and the detector to lock the detector in 6 degrees-of-freedom at predefined arresting locations.

9. The system according to claim 8, wherein the detector is coupled to three arresting elements, each of which includes a groove that receives a respective arresting sphere at an arresting location.

10. The system according to claim 9, wherein each groove is orthogonal to each other groove on the arresting elements, such that the three grooves correspond to three orthogonal planes, and wherein the detector is prevented from moving backwards or forwards in each of the three orthogonal planes with the three arresting spheres are mated with the respective three arresting elements.

11. The system of claim 1, further including a processor that executes computer-executable instructions comprising:
   acquiring the CT data of the subject;
   reconstructing the CT data into the 3D image representation having a 3D array of voxels, each voxel having a gray-scale value;
   identifying the voxels corresponding to blood; and
   generating the 3D volume image of vasculature in the subject using the identified blood voxels.

12. A method of performing neo-vasculature quantification in a subject, including:
   performing a CT scan on the subject to acquire CT data of the subject;
   reconstructing, via a reconstruction processor, the CT data into 3D image representation having a 3D array of voxels, each voxel having a gray-scale value;
   calibrating the gray-scale values of the voxels in the 3D image representation to Hounsfield units;
   identifying voxels having Hounsfield units corresponding to blood, as the blood voxels;
   generating a 3D volume image of vasculature in the subject from the identified blood voxels;
   generating a 3D blood vessel vasculature volume image;
   calculating a medial axis of vessels in the blood vessel volume image;
   stepping along a blood vessel medial axis;
   at each step, measuring a diameter of the blood vessel;
   generating a histogram of the number of steps with each measured diameter;
   generating a 3D expansion of the 3D vasculature image;
   comparing each blood vessel diameter measurement with a predetermined blood vessel diameter value range that includes a lower level indicative of blood vessel diameter consistent with a predefined capillary diameter and an upper level indicative of blood vessel diameter consistent with a predefined artery diameter;
   automatically terminating expansion of the 3D vasculature image along a given path when the number of laterally adjacent blood voxels falls outside the predetermined blood vessel diameter value range;

automatically generating a 3D volume rendering of the 3D volume image representation of the vasculature upon termination of the expansion of the 3D vasculature image; and displaying the 3D volume rendering of the 3D volume image representation of the vasculature.

13. The method according to claim 12, further including:

scanning a Hounsfield calibration phantom, in a subject support, during CT data acquisition, to collect calibration information;

the calibration phantom including an air, a water, and a bone equivalent material.

14. The method according to claim 13, further including:

determining a ratio of blood vessel volume from a volume of a tumor in the 3D image representation and a number of blood voxels in the tumor volume.

15. The method according to claim 12, further including:

calculating a volume of the blood vessels;

calculating a volume of a volume of interest; and calculating a ratio.

* * * * *